United States Patent
Hossain et al.

Patent Number: 6,067,154
Date of Patent: May 23, 2000

[54] METHOD AND APPARATUS FOR THE MOLECULAR IDENTIFICATION OF DEFECTS IN SEMICONDUCTOR MANUFACTURING USING A RADIATION SCATTERING TECHNIQUE SUCH AS RAMAN SPECTROSCOPY

[75] Inventors: Tim Z. Hossain; Charles E. May, both of Austin, Tex.

[73] Assignee: Advanced Micro Devices, Inc., Sunnyvale, Calif.

[21] Appl. No.: 09/177,930

[22] Filed: Oct. 23, 1998

[51] Int. Cl.$^7$ ..................................................... G01N 21/00
[52] U.S. Cl. ........................................ 356/237.2; 356/301
[58] Field of Search .............................. 356/237.1–237.6, 356/399–401, 301, 369; 250/559.45, 559.09, 559.16, 225

[56] References Cited

U.S. PATENT DOCUMENTS 4,978,862  12/1990  Silva et al. .
5,208,648   5/1993  Batchelder et al. .

OTHER PUBLICATIONS

Clark et al. "Dynamic . . . Inspection", J. Vac. Sci Technol. B 10(6) Nov. 12, 1992 pp. 2638–2642.
Skoog et al., "Raman Spectroscopy," *Principles of Instrumental Analysis*, 5th Ed., Chapter 18, 1992.

Primary Examiner—K. P. Hantis
Attorney, Agent, or Firm—Kevin L. Daffer; Conley, Rose & Tayon

[57] ABSTRACT

A method and apparatus are provided for obtaining molecular information about materials at a selected site on or in a semiconductor topography. In a preferred embodiment, the selected site is a defect from a defect map generated by an automated wafer inspection system. A sample stage and drive/alignment system are used to move the semiconductor topography such that a selected defect is aligned with the illumination provided by a radiation scattering measurement system. A Raman spectroscopy system may be used for the radiation scattering measurement. The intensity and frequency of inelastically scattered radiation from the vicinity of the selected defect is compared to standard spectra to determine the chemical composition and material phase of the region analyzed. The depth into the topography probed may be adjusted by changing the wavelength of radiation used in the Raman spectroscopy measurement. In this way, the source of a particular defect, even if buried in the topography during the semiconductor fabrication process, may be determined. Knowledge of the fabrication process guides selection of the appropriate depths to be analyzed.

15 Claims, 9 Drawing Sheets

METHOD AND APPARATUS FOR THE MOLECULAR IDENTIFICATION OF DEFECTS IN SEMICONDUCTOR MANUFACTURING USING A RADIATION SCATTERING TECHNIQUE SUCH AS RAMAN SPECTROSCOPY

BACKGROUND OF THE INVENTION

1. Field of the Invention

This invention relates to the field of semiconductor wafer fabrication and, more specifically, to an apparatus and method for obtaining nondestructive molecular characterization of manufacturing defects within a semiconductor topography using inelastic scattering of incident monochromatic radiation.

2. Description of the Relevant Art

Scrupulously clean wafers are critical for obtaining high yields in the manufacture of integrated circuits with submicron device dimensions. The small feature sizes and the thinness of layers deposited on the surfaces of semiconductor wafers during the manufacture of such devices makes the process extremely vulnerable to damage caused by manufacturing defects. These manufacturing defects can degrade the performance or reliability of produced devices, and may even render a significant number of devices formed upon contaminated surfaces of semiconductor wafers inoperative.

General categories of semiconductor wafer defects include particles, films, and structural defects. Particles are any tiny pieces of foreign material that have readily discernible boundaries. Sources of particulate contamination include dust in the air, lint from clothing worn by clean room personnel, particles present in processing chemicals, and particles generated by processing equipment. Film contaminants form layers of foreign material on surfaces of semiconductor wafers. Examples of film contaminants include solvent residues, photoresist developer residue, oil films, and metallic films deposited during procedures involving immersion of wafers in a liquid. Structural defects include scratches, mounds, dimples, stacking faults and slip lines, and typically do not differ in chemical composition from the material immediately surrounding them.

In order to produce devices with acceptable performance and reliability characteristics, manufacturing defects must be detected. Optical microscopy can be used to detect particles down to about 0.5 microns in diameter, as well as the presence of scratches and solvent residues on wafer surfaces. Automated wafer inspection systems, such as those manufactured by KLA-Tencor, are now widely used in the semiconductor manufacturing industry for detection of defects, particularly particles and structural defects. These systems employ various illumination and image processing techniques, such as laser reflection from unpatterned wafers or subtraction of images from repeated structures on a patterned wafer (die-to-die comparison). Output generated by KLA-Tencor wafer inspection systems typically includes a defect map of a wafer, containing information on the size and location of defects present.

Once the presence of a manufacturing defect is detected, further analysis of the defect is needed. Information on the structure and chemical composition of a defect may enable removal of the defect during the process and preservation of the performance of the devices being manufactured. More importantly, however, information gained from analysis of a manufacturing defect aids in identification and elimination of the defect source, so that future occurrences of the defect are prevented. In order to determine the origin of particular defects, it is often desirable to examine product wafers (i.e., wafers expected to yield operational devices) before and after selected processing steps. Nondestructive analysis techniques are therefore needed.

Currently used analysis methods usually provide information on either the physical structure or elemental composition of defects. Non-destructive techniques of structural analysis commonly used in wafer fabrication include optical microscopy and scanning electron microscopy (SEM). A scanning electron microscope directs a beam of primary electrons at the surface of a wafer and detects emitted secondary electrons in order to form an image of the wafer surface. Another structural analysis technique which is being increasingly used in semiconductor characterization is scanning probe microscopy (SPM). SPM comprises a family of techniques in which a probe is held extremely close to a surface and scanned with high resolution and accuracy (tenths of nanometers). Some interaction between the probe and the surface is then measured. In the case of scanning tunneling microscopy, for example, tunneling current is measured. The most commonly-used SPM technique in characterization of semiconductor fabrication is atomic force microscopy (AFM), in which the force between the probe and surface is measured. Typical applications include measurement of roughness, pinholes, and other topographical features on a wafer.

Nondestructive techniques commonly used for elemental analysis include Auger emission spectroscopy (AES) and X-ray fluorescence spectroscopy (XRF). Like SEM techniques, AES techniques involve directing a beam of primary electrons at the surface of a wafer. Instead of forming an image using detected secondary electrons emitted by atoms on the upper surface of a wafer, AES techniques measure the energy levels of the emitted electrons to determine elemental compositions of surface structures. In XRF techniques, a beam of primary X-rays is directed at the surface of a semiconductor wafer, and the energy levels (or corresponding wavelengths) of resultant secondary X-rays emitted by atoms of elements on and just under the surface of the wafer are measured. Atoms of elements in target materials emit secondary X-rays with uniquely characteristic energy levels (or corresponding wavelengths). Thus the elemental compositions of materials on and just under the surface of the wafer may be determined from the measured energy levels (or wavelengths) of emitted secondary X-rays.

Although the above-described techniques are useful for defect analysis in semiconductor manufacturing, none of them are capable of providing molecular identification of defects. For example, a technique such as AES or XRF might identify the presence of the elements silicon and nitrogen in a defect, but would not be able to determine that these atoms were in, for example, a silicon oxynitride layer having a particular chemical composition. Knowledge of the actual chemical compounds present in a defect can be extremely valuable in identifying the mechanism through which the defect was formed. This is particularly important in the case of deposition processes, in which precursor materials, such as tetraethyl orthosilicate (TEOS), often consist of large molecules which may participate in complex chemical reactions on the wafer surface during a deposition.

Infrared (IR) absorption spectroscopy is a commonly-used nondestructive technique for obtaining molecular identification of materials. IR absorption spectroscopy involves detecting molecular vibrations, or vibrations characteristic of atoms which are bonded together. Incident radiation which has the same frequency as a molecular vibration in the material is absorbed. The result of the measurement is typically a plot of transmitted radiation intensity versus wavenumber (reciprocal of wavelength) of the radiation, showing many transmission dips corresponding to vibrational mode frequencies. Coupling between vibrations involving different parts of a molecule results in a complex spectrum which provides a distinctive signature for the particular chemical compound and phase being measured. A very popular instrument for performing infrared absorption measurements is the Fourier transform infrared (FTIR) spectrometer. In an FTIR spectrometer, transmittance (or absorption) is measured at all frequencies of the spectrum simultaneously, using interferometry and Fourier transform techniques. This results in an ability to average many measurements in a short time and realize significant improvements in signal-to-noise ratio.

A problem arises with FTIR and other IR absorption measurements for analysis of defects in semiconductor fabrication, however, because of the spot size of the incident beam. Wavelengths of the vibrations used for identification of most chemical compounds are in the mid-infrared region, from approximately 2 microns to 25 microns. Because the wavelength of the incident radiation must match that of the vibrations to obtain an absorption spectrum, the incident radiation used in IR absorption measurements is also in the wavelength range of 2 microns to 25 microns. The spot size of a beam of radiation is related to its wavelength such that the lower limit of the spot size is on the order of the wavelength. Therefore, the area illuminated by the incident radiation in an IR absorption measurement, and the area from which the resulting absorption signal is collected, can be on the order of 25 microns in diameter. Because many semiconductor manufacturing defects are of submicron size, this illumination area is much too large for isolation of a particular defect for analysis. To be useful for analysis of submicron-sized defects, an illumination area having a diameter of no more than approximately one micron is needed.

Even the ability to obtain molecular identification of a small region surrounding a defect is of limited utility without a technique for finding and focusing on a selected defect. Manual searching for defects using a microscope is extremely time-consuming and tedious, and submicron defects may not be visible by optical microscopy. A scanning probe microscope obtainable from Digital Instruments, model Dimension 7000, with the capability to import defect maps from KLA-Tencor wafer inspection systems and move its scanning probe to the site of a chosen defect has been advertised. There is, however, no known apparatus by which semiconductor manufacturing defects can be found and analyzed by a method providing nondestructive molecular identification.

During fabrication of an integrated circuit, various materials are grown from, deposited onto, or introduced into a semiconductor substrate. The resulting semiconductor topography, including the substrate and the overlying layers, changes throughout the process. A defect formed during one step of a fabrication process may be buried during subsequent steps, so that examination of manufacturing defects should not be confined to analysis of the surface of the semiconductor topography.

It would therefore be desirable to develop an apparatus and method for finding and obtaining nondestructive molecular identification of semiconductor manufacturing defects. To be useful for analysis of submicron-sized defects, the apparatus should allow analysis of an area as small as approximately one micron in diameter. The apparatus should also have the capability to controllably analyze material below the surface of a semiconductor topography. Moreover, the apparatus must have the capability to locate and focus on a chosen defect for analysis.

SUMMARY OF THE INVENTION

An apparatus and method for obtaining molecular identification of material from selected sites on or in a semiconductor wafer are described herein. Broadly speaking, the apparatus combines a system which detects the intensity and frequency of radiation scattered from a semiconductor substrate with a system for aligning incident radiation with a selected site on the substrate. In a preferred embodiment, the selected site corresponds to a defect from a defect map of the substrate generated by an automated wafer inspection system. The system for detection of scattered radiation may take the form of a Raman spectroscopy system. The phrase "Raman spectroscopy" as used herein is also intended to refer to any measurement of intensity and frequency of scattered radiation which is used to obtain molecular identification of a material. A method is also described which uses the apparatus recited herein in combination with knowledge of the fabrication process performed on the substrate to identify the source or sources of a defect found on the semiconductor surface.

In a Raman spectroscopy measurement, radiation which is scattered by molecular vibrations is detected. Monochromatic radiation from a laser is incident upon a sample to be analyzed. Radiation which is scattered by the sample is then detected. Most of the radiation is elastically scattered, so that it undergoes no change in energy or frequency during the scattering process. If molecular vibrations exist which change the polarizability of a molecule, however, a small fraction of the radiation will be inelastically scattered. Such vibrations are said to be "Raman active". An intensity vs. wavenumber plot of the scattered radiation obtained using a monochromator and detector will comprise a large peak at the wavenumber of the incident radiation, and a group of small peaks on either side of the large peak, both at higher and lower wavenumbers. The difference between the wavenumber of a Raman peak and that of the incident radiation corresponds to the frequency of the associated vibrational mode. As in the case of IR absorption spectroscopy, discussed above, a distinctive signature for a given compound and phase results. Raman spectroscopy, however, has the feature that the frequency of the incident radiation does not need to match that of the vibrational modes being detected. Since it is the change in frequency of the scattered radiation that is measured, the incident laser radiation can be at a much higher frequency than that of the vibrational modes. This higher frequency, shorter wavelength radiation can be focused to small spot sizes on the sample being analyzed.

The apparatus disclosed herein preferably uses Raman spectroscopy in the Raman microprobe configuration, in which microscope optics and/or optical fibers are used to focus the incident laser radiation to a spot size of approximately 1 micron, and to collect the scattered radiation from the immediate vicinity of the radiated spot. In this way, very small areas of a sample may be analyzed. The depth to which the analyzed region of the sample extends depends on the penetration depth of the laser radiation, which is in turn dependent on to what extent the radiation is absorbed by the sample. Because absorption effectiveness depends on the energy of the incident radiation, with higher-energy radiation absorbed more strongly, the penetration depth of the radiation may be changed by changing its energy. Therefore, analysis of defects on semiconductor wafers may be enhanced when using a Raman spectroscopy system by variation of the energy of the incident radiation. For example, analysis may be restricted to the sample surface for examination of surface defects such as freshly-deposited particles, or performed at an increased depth to examine defects which may extend below the surface of the topography.

The apparatus includes a sample stage which holds the semiconductor topography for analysis by the Raman spectroscopy system (or other scattered radiation detection system). The sample stage is connected to a drive/alignment system which moves the stage in the horizontal plane for alignment of the semiconductor topography such that a selected defect is illuminated by the incident radiation from the Raman spectroscopy system. Raman-scattered radiation can then be collected from the region including the selected defect and detected using a monochromator. The resulting spectrum may then be interpreted to identify the chemical compounds present in and around the defect. The drive/alignment system includes a laser and detector for implementing a laser reflection technique of aligning the semiconductor topography to establish an initial reference position. The drive/alignment system also includes motors and/or piezoelectric elements to move the sample stage in x and y directions within the horizontal plane, and to rotate the sample stage in the horizontal plane.

A computer system is connected to and in communication with the drive/alignment system and the Raman spectroscopy system. In a preferred embodiment, the computer system is used to control the drive/alignment system and the Raman spectroscopy system. Programs which run on the computer system allow it to import a defect map generated by an automated wafer inspection system for a semiconductor topography. Locations of selected defects, or other locations to be analyzed, are also entered using the computer system. The computer system communicates these locations to the drive/alignment system, which moves the semiconductor topography such that the selected location is aligned with the Raman system. The apparatus may also include computer software which causes the drive/alignment system to scan areas of a wafer and causes the Raman spectroscopy system to make measurements during the course of the scan. In this way, defects may be detected on an unmapped wafer using results of the Raman spectroscopy measurements.

It should be noted that the SPM system described above which has been advertised as also having capability to import a defect map is believed dissimilar from the apparatus disclosed herein. In the case of an SPM system, relatively little modification is required to enable alignment of the measurement system with a selected defect, because SPM is inherently a scanning-based measurement. Measured data is essentially always obtained versus position, either as a line scan or an x-y scan. Therefore, scanning hardware and software is included in the basic configuration of the system. Raman spectroscopy, on the other hand, is not inherently a scanning-based measurement. Information about the composition of a sample may be obtained from a measurement at a single position, in which intensity versus wavenumber of Raman-scattered radiation is recorded. The basic configuration of a Raman spectroscopy system would therefore not necessarily include scanning hardware and software. The modification required to align a selected defect with the illumination area of a Raman spectroscopy system may be considerably greater than that required in the case of SPM. Furthermore, Raman spectroscopy is not currently a commonly used tool in semiconductor manufacturing environments. The replacement of an SPM with a Raman spectroscopy system when examining defects mapped by an automated wafer inspection system therefore presents many challenges which the present solution addresses.

Furthermore, the apparatus recited herein is intended for use in a substantially different manner than that of an AFM or other SPM. In particular, the ability to vary the depth analyzed using Raman spectroscopy coupled with knowledge of the intended layer structure at a given point in a semiconductor manufacturing process provides a powerful means of determining the source of a defect. With an AFM, on the other hand, only information about the surface physical structure of a defect is available.

A method for obtaining molecular identification of material at a selected site within a semiconductor topography is further contemplated herein. In a preferred embodiment of the method, a defect map for a substrate is acquired using an automated wafer inspection system. One or more defects are subsequently selected for analysis. From knowledge of the semiconductor fabrication process which has been applied to the substrate, the user determines which layer or layers the selected defects are on or above. This knowledge aids in choosing the depth into the substrate at which analysis is to be performed. The frequency of a monochromatic radiation source, preferably a laser, is chosen to provide the desired penetration depth into the substrate. The substrate is loaded onto the sample stage of the apparatus recited herein, and the sample stage is moved so that the selected defect is aligned with the area on the substrate surface which is illuminated by the monochromatic radiation sources The surface defect and underlying material are then illuminated, while the intensity and frequency shift of the resultant scattered radiation are detected. The intensity versus frequency shift of the scattered radiation is compared to standard spectra for identification of the molecular composition of material in or under the defect. The analysis may be repeated using different frequencies of incident radiation in order to identify the compositions of material at a range of depths and assist in identifying the source of the defect. The entire procedure may further be repeated using other selected defects.

BRIEF DESCRIPTION OF THE DRAWINGS

Other objects and advantages of the invention will become apparent upon reading the following detailed description and upon reference to the accompanying drawings in which.

Figure 1:
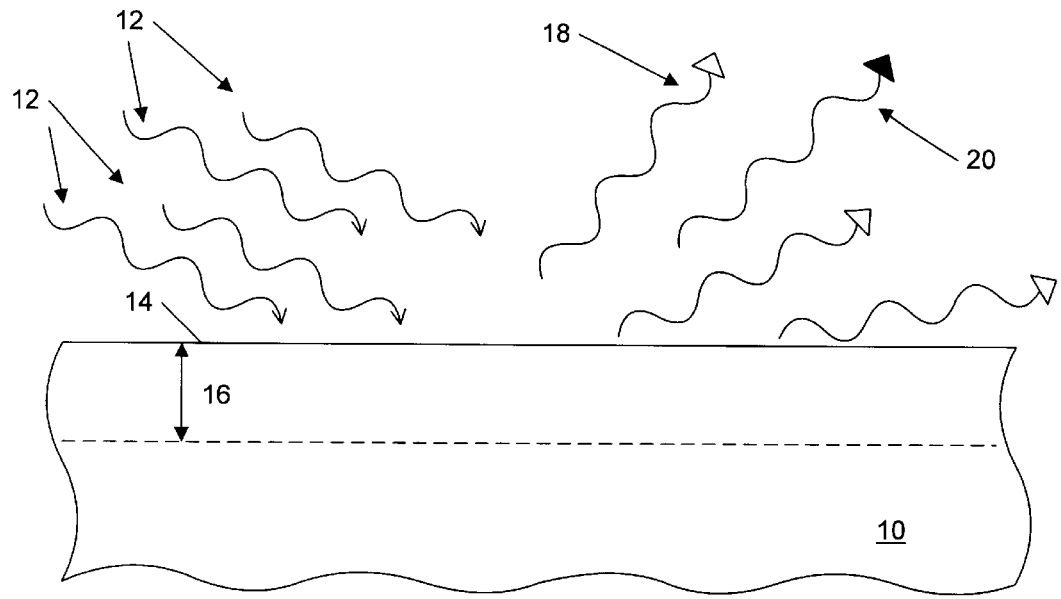
FIG. 1 is a partial cross-sectional view of a semiconductor substrate in which monochromatic radiation is scattered.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed. On the contrary, the intention is to cover all modifications, equivalents, and alternatives falling within the spirit and scope of the present invention.

DETAILED DESCRIPTION OF THE PREFERRED EMBODIMENTS

Turning to the drawings, a substrate 10 in which radiation scattering is occurring is shown in FIG. 1. Incident photons 12 from a monochromatic radiation source impinge upon upper surface 14 of substrate 10. The distance into substrate 10 traveled by the photons, on average, before they are absorbed by the semiconductor is the penetration depth 16. Penetration depth 16 is dependent on the energy of incident photons 12, with higher-energy radiation being absorbed more strongly and having a smaller penetration depth. Some of the photons will be scattered by atoms and molecules within the volume bounded by penetration depth 16 of substrate 10, and re-emerge through upper surface 14. Of these scattered photons, most are elastically scattered photons 18 (shown with open triangular arrowheads in FIG. 1) which have the same frequency as incident photons 12. A small fraction of the scattered radiation (typically about 1/1000), however, is scattered such that the frequency of the scattered radiation is shifted from that of the incident radiation. This fraction is represented by inelastically scattered photon 20, shown with a filled triangular arrowhead in FIG. 1.

Figure 2:
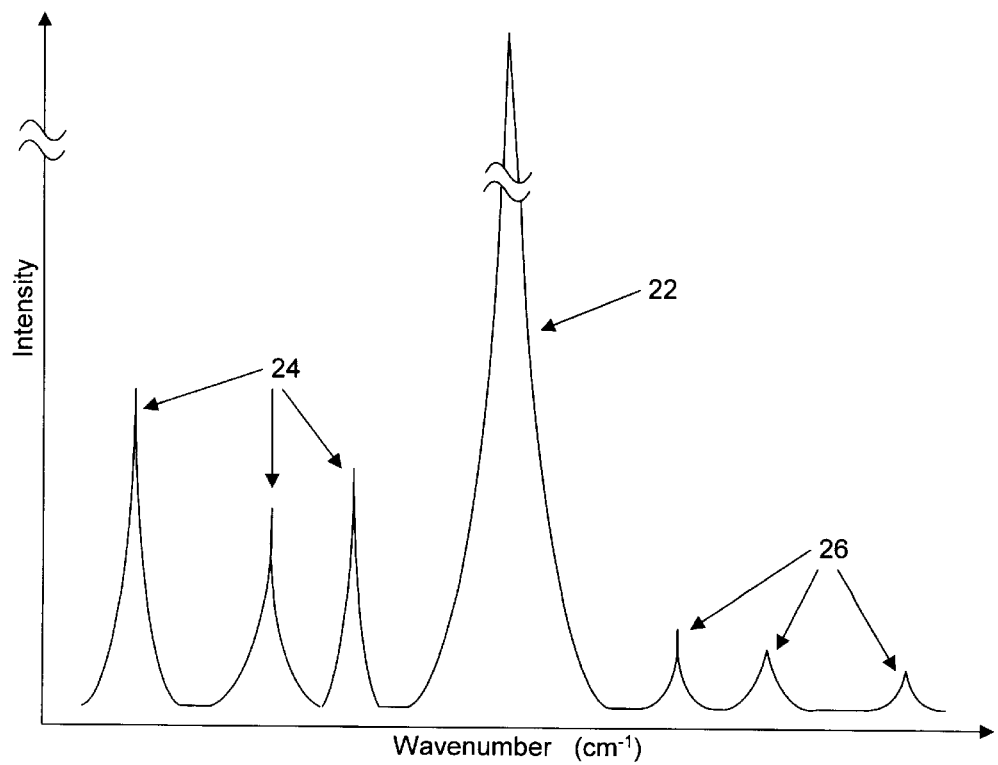
FIG. 2 is a plot of intensity vs. wavenumber for an exemplary radiation scattering measurement.

Inelastically scattered photons such as photon 20 are of interest because the frequency shifts experienced by these photons are related to molecular vibrations in the scattering material. Coupling between vibrations involving different parts of a molecule and/or a solid results in a complex relationship between frequency shift and intensity of inelastically scattered radiation. A representative intensity vs. wavenumber plot for a Raman spectroscopy experiment is shown in FIG. 2. In a Raman spectroscopy experiment, monochromatic radiation is directed into a sample, and the intensity and frequency shift of scattered radiation is detected, as discussed above. The frequency shift in a Raman spectrum is often plotted in terms of a shift in wavenumber, where wavenumber is the reciprocal of the wavelength, in units of $cm^{-1}$. For the spectrum of FIG. 2, peak 22 represents radiation which is elastically scattered, or Rayleigh scattered. Elastically scattered radiation peak 22 is much more intense than other peaks in a spectrum, typically on the order of one thousand times more intense. Peaks 24 at lower wavenumbers than peak 22 are called Stokes radiation peaks. Stokes peaks 24 correspond to inelastically scattered photons which are shifted to lower frequencies. The peaks 26 at higher wavenumber than peak 22 correspond to inelastically scattered photons which are shifted to higher frequencies, and are called anti-Stokes radiation peaks.

Stokes scattering may be described as resulting from an interaction between a photon and a molecule which is in its lowest, or "ground", electronic state. If the interaction with the photon leaves the molecule in a vibrational mode, corresponding to a higher, or excited, electronic state, the energy gained by the molecule is lost by the photon. This energy loss by the photon corresponds to a lowering of photon frequency, and the photon has therefore been Stokes scattered. Anti-Stokes scattering, on the other hand, results from an interaction between a photon and a molecule which is in an excited state corresponding to a vibrational mode. If the interaction with the photon leaves this molecule in its ground state, the energy lost by the molecule is gained by the photon, which is thereby anti-Stokes scattered. Because the population of molecules in an excited electronic state is small compared to that of molecules at ground state, the intensities of Stokes peaks such as peaks 24 are always greater than those of anti-Stokes peaks such as peaks 26. For this reason, Raman spectra are often plotted to include only Stokes peaks 24. The intensities and wavenumber shifts of the Stokes peaks may be compared to reference spectra for unique identification of the composition and phase (crystalline, amorphous, liquid, etc.) of the scattering material. Anti-Stokes peaks may also be used, however, particularly in cases for which other optical processes in a material produce peaks which interfere with Stokes radiation.

Figure 3:
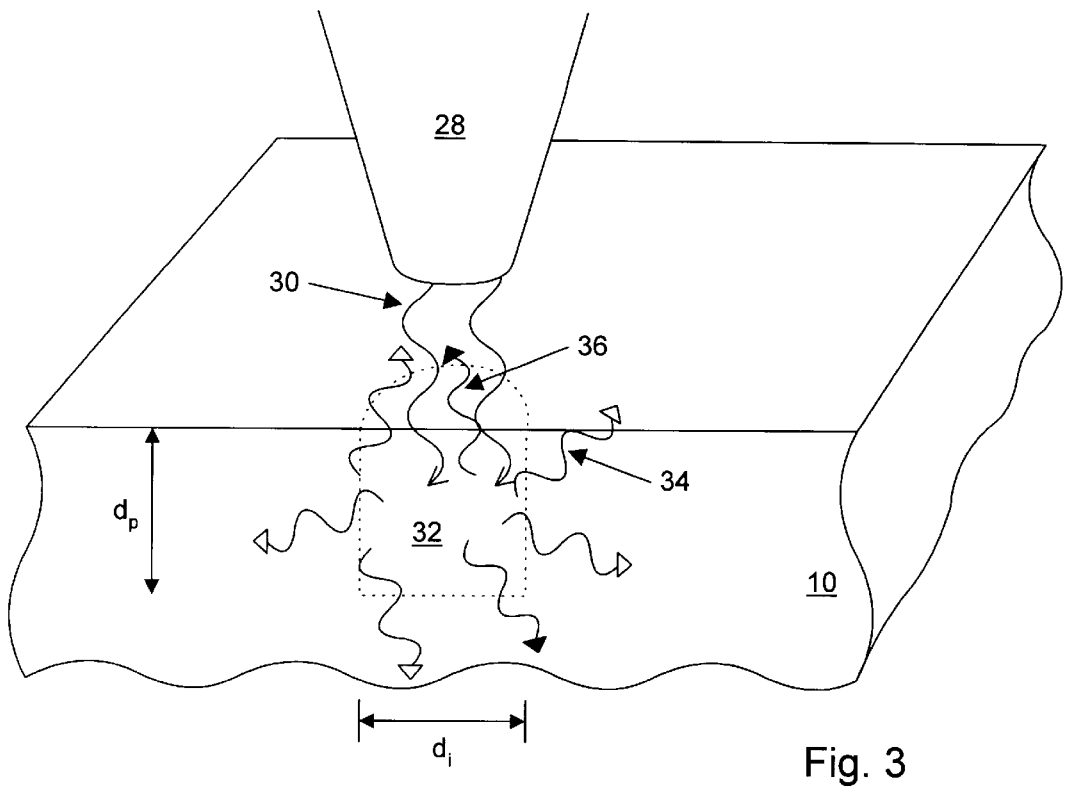
FIG. 3 is a partial cross-sectional perspective view of the radiation scattering geometry of a typical Raman microprobe system.

Turning now to FIG. 3, a sample illumination geometry for a Raman microprobe spectroscopy system is shown. Microscope objective 28 may be used to focus incident monochromatic photons 30 onto substrate 10. Illuminated portion 32 of substrate 10, having a boundary shown by a dashed line in FIG. 3, has a diameter $d_i$ and a depth $d_p$ (corresponding to the penetration depth of the light). Diameter $d_i$ of illuminated region 32 is typically as small as about one micron. Penetration depth $d_p$ is related to the frequency of the illuminating radiation and the substrate material. Penetration depths in a silicon substrate can range from a few angstroms to a few tens of microns, depending on the radiation wavelength used. Although illuminated region 32 is shown in FIG. 3 as having uniform diameter with depth into the substrate, some spreading of the illuminated region below the surface of the sample may occur. Causes of such spreading may include diffusion and/or scattering of photons. Within illuminated region 32, photons may be scattered in all directions. Those photons which scatter back into microscope objective 28 are detected by the Raman spectroscopy system. As in FIG. 1, elastically scattered photons are indicated by open triangular arrowheads and inelastically scattered photons are indicated by filled triangular arrowheads. Photon 34, for example, is elastically scattered in such a direction that it is not collected by microscope objective 28. Photon 36 is inelastically scattered in a direction that does allow it to be collected by objective 28. Photon 36 may therefore contribute to an intensity vs. wavenumber shift spectrum produced for the sample.

Figure 4:
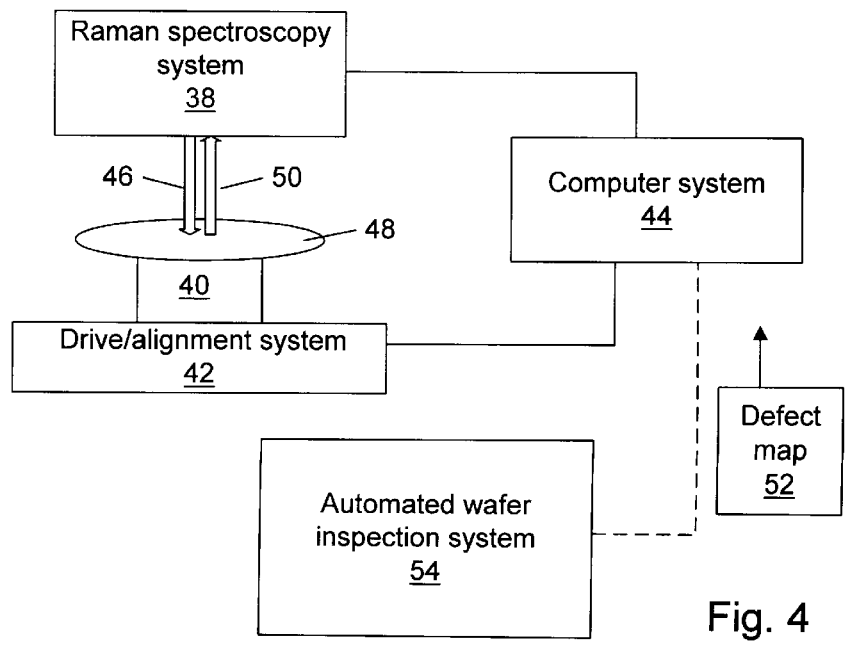
FIG. 4 is a side elevation view of an embodiment of the apparatus recited herein.

A side elevation view of an embodiment of the apparatus recited herein for obtaining molecular identification of material from a selected sites on or in a semiconductor wafer is shown in FIG. 4. In this embodiment, molecular identification of material in a wafer, or substrate, is accomplished using Raman spectroscopy. Components of the apparatus include Raman spectroscopy system 38, sample stage 40, drive/alignment system 42, and computer system 44. Incident radiation beam 46, represented by a hollow arrow in FIG. 4, is directed onto semiconductor topography 48 by Raman spectroscopy system 38. Semiconductor topography 48 includes a semiconductor substrate, or wafer, and may also include other materials on or in the substrate. These materials could include insulating layers, conductive layers, dopant atoms, solvents, polymer layers, and/or other materials used in semiconductor manufacturing. In other words, topography 48 preferably includes a semiconductor substrate at some stage of an integrated circuit fabrication process. Radiation beam 50 contains scattered radiation which is collected by Raman system 38. Topography 48 is mounted on sample stage 40, which is moved by drive/alignment system 42 such that a selected site to be analyzed on topography 48 is aligned with incident radiation beam 46. Computer system 44 is used to control operation of the apparatus, including in particular the Raman spectroscopy system and the drive/alignment system. Computer system 44 includes a processor, data storage, an input device, and a display device. Defect map 52, generated by automated wafer inspection system 54, may be imported into computer system 44. Automated wafer inspection system 54 is similar to systems available from companies such as KLA/Tencor.

Techniques used by inspection system 54 to detect defects on surfaces of semiconductor substrates may include laser reflection, typically used on unpatterned wafers, and die-to-die image comparison for patterned wafers. After detection of defects, defect map 52 may then be generated by inspection system 54. Defect map 52 typically includes x-y coordinates of detected defects, and may include other information such as sizes of defects.

The solid lines shown connecting computer system 44 to Raman system 38 and drive/alignment system 42 in FIG. 4 preferably represent physical connections between these elements. These connections may include electrical or optical data lines and/or control signal lines. The dashed line shown between computer system 44 and wafer inspection system 54 in FIG. 4 may represent a physical connection, such as a computer networking cable by which defect map 52 in transmitted. Alternatively, defect map 52 may be imported into computer system 44 without a permanent connection between the two. Because computer system 44 may not be located in close proximity to wafer inspection system 54, such an arrangement may be more convenient. For example, defect map 52 may be brought to computer system 44 using a data diskette. Information on specific defects from defect map 52 may even be entered into computer system 44 without importing the entire defect map.

Figure 5:
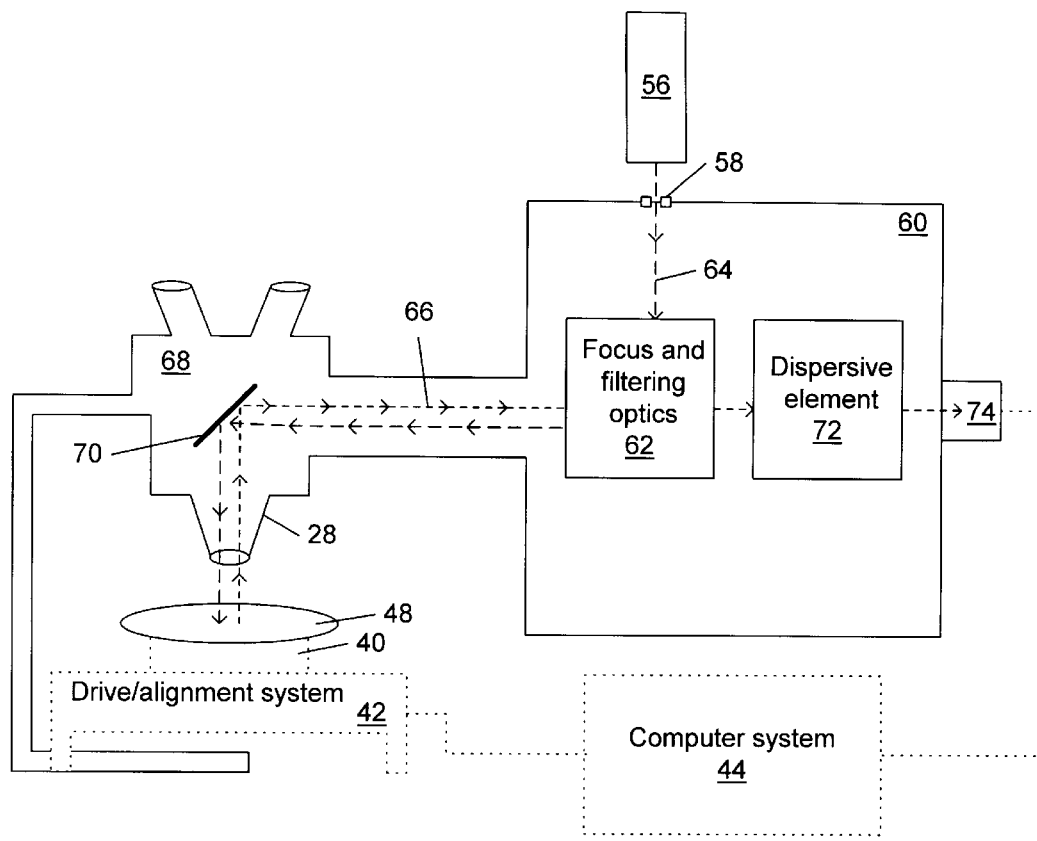
FIG. 5 is a side elevation view of an embodiment of the system for scattered light detection included in FIG. 4.

A side elevation view of an embodiment of Raman spectroscopy system 38 of FIG. 4 is shown in FIG. 5. In the embodiment of FIG. 5, a Raman microprobe configuration is used. The small illumination region diameter achievable, about one micron, makes a microprobe configuration appropriate for analysis of many of the defects found on semiconductor substrates. Radiation from monochromatic optical source 56 is directed through entrance slit 58 into monochromator unit 60. Monochromatic optical source 56 is preferably a laser. Monochromatic radiation may also be achieved using a broadband radiation source such as a filament lamp combined with a filter, grating or other element which selects a single frequency. Such an arrangement may not provide sufficient signal power, however. Preferred lasers for use as optical source 56 include argon ion lasers, krypton ion lasers, helium-neon lasers, and tunable titanium:sapphire lasers. Monochromator unit 60 typically includes a wavelength-dispersive element, such as a prism or grating, and beam-conditioning optics such as lenses and/or filters. In the embodiment shown in FIG. 5, a grating monochromator is used. Although radiation from monochromatic optical sources such as source 56 is nominally monochromatic, it is typically passed through a monochromator unit such as 60 for further beam conditioning. In the embodiment of FIG. 5, radiation from optical source 56 passes through focus and filtering optics 62 on the way to microscope 68.

Incident optical path 64, taken by the monochromatic radiation to reach semiconductor topography 48, is shown in FIG. 5 with a long-dashed line having arrows to show direction. Return optical path 66, shown with a short-dashed line, is taken by the scattered radiation collected by microscope 68. After passing through optics 62, incident optical path 64 enters microscope 68 which typically contains at least one mirror 70 to direct incident radiation through microscope objective 28 to semiconductor topography 48. Radiation scattered in topography 48 which is collected by objective 28 travels along return optical path 66. An exemplary scattering geometry is shown in more detail in FIG. 3. Return optical path 66 follows incident path 64 back through microscope 68 and optics 62. Optics 62 may help to remove any "stray light" which may have entered the system from the scattered radiation before detection. Return path 66 goes from optics 62 to dispersive element 72, which preferably includes a grating and one or more mirrors. Alternatively, a prism or other wavelength-dispersing element may be used. The grating or other dispersive element separates in space the various wavelengths of the scattered radiation. The dispersed radiation is then collected by detector 74. In a preferred embodiment, detector 74 is a multichannel detector such as a charge-coupled device (CCD) camera. In this case, the entire spatial pattern formed by the dispersed radiation may be detected simultaneously. Other multichannel detectors, such as photodiode arrays, may also be usable for detector 74. Alternatively, detector 74 may be a single-channel detector which is exposed to the scattered radiation one wavelength increment at a time, by, for example, scanning a grating to sequentially align parts of a dispersed radiation pattern with a slit between the dispersive element and the detector. Single-channel detectors which may be used in such an arrangement include photomultiplier tubes and photodiode detectors such as Ge detectors. If a photodiode detector is used, the radiation to be detected must generally have higher energy than the bandgap of the detector material.

Other apparatus components which connect to the Raman spectroscopy system, including sample stage 40, drive/alignment system 42, and computer system 44, are shown in phantom in FIG. 5. Intensity data from detector 74 is preferably transferred to computer system 44, where it is plotted with respect to frequency or wavenumber for comparison to standard spectra and identification of the material or materials analyzed. If a scanned dispersive element is used, computer system 44 may control the scan and sequentially collect intensity vs. wavelength data. If a multichannel detector is used, computer system 44 may convert the positions in the detector array at which photons are detected to wavelength (or frequency) using system calibration information. A separate control unit may also be included in Raman spectroscopy system 38. Such a unit may, for example, control any dispersive element scanning which may be necessary, and may communicate with computer system 44. Items not shown in FIG. 5 include power supplies for elements such as optical source 56 and detector 44, and one or more light-blocking enclosures surrounding all of optical paths 64 and 66, including microscope 68 and topography 48.

Figure 6:
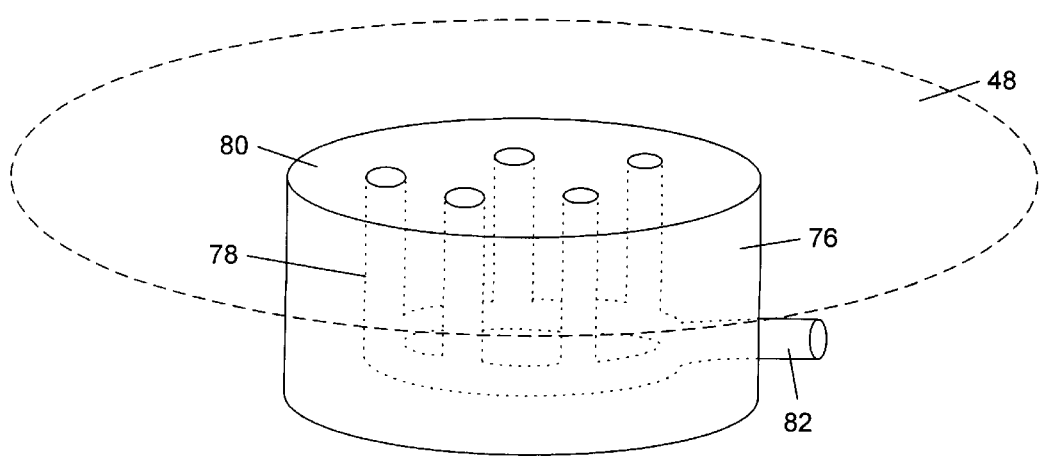
FIG. 6 is a perspective view of an embodiment of the sample stage included in FIG. 4.

Turning now to FIG. 6, a side elevation view of an embodiment of sample stage 40 of FIG. 4 is shown. In this embodiment, sample stage 40 is a disk 76 upon which semiconductor topography 48, shown in phantom in FIG. 6, may rest. Channels 78 formed in the interior of disk 76 allow use of a vacuum to hold topography 48 against upper surface 80 of disk 76. The vacuum may be established by attaching a vacuum line to connector 82 after topography 48 is placed onto disk 76. Disk 76 should be formed from a material strong enough to support formation of channels 78 and application of a vacuum through channels 78. Furthermore, the material used to form disk 76 should be capable of being made substantially clean and particle-free, so that contamination of semiconductor topography 48 during analysis by the apparatus is minimized. Materials which may be suitable for formation of disk 76 include metals and polymeric materials such as TEFLON. In an alternate embodiment, sample stage 40 may be larger in diameter than topography 48, and may include features such as notches or ridges to aid in alignment of topography 48. Instead of a vacuum, alternative methods, such as mechanical clips, of fixing topography 48 to sample stage 40 may be used.

Figure 7:
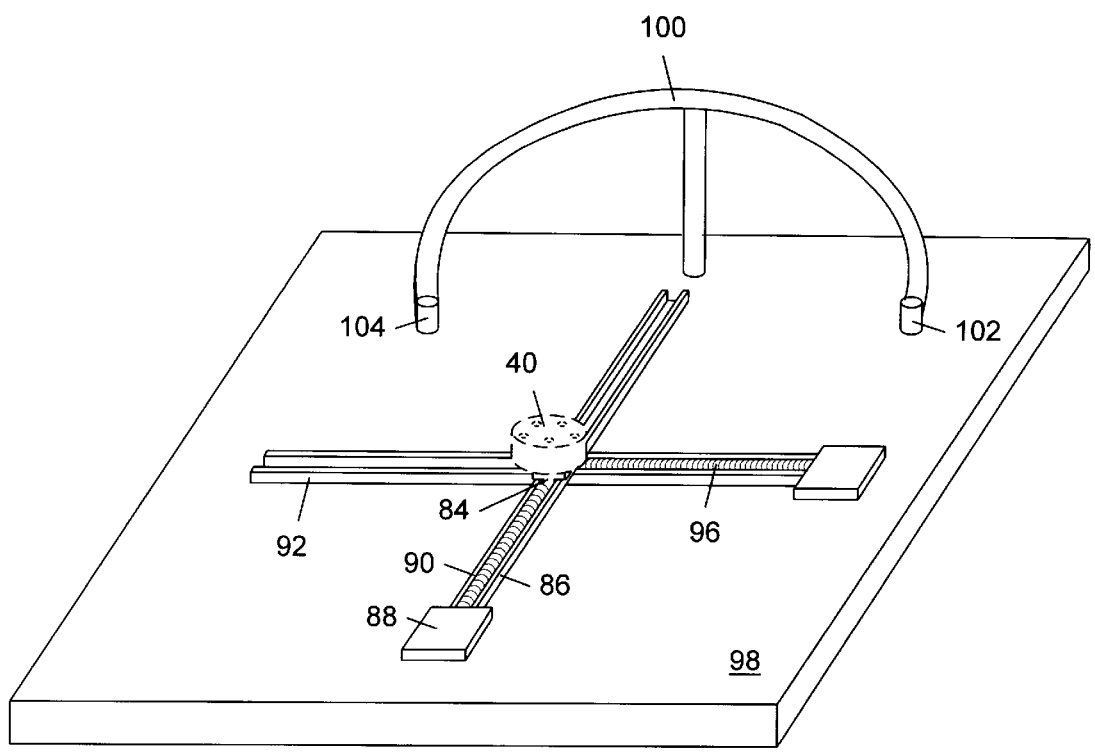
FIG. 7 is a perspective view of an embodiment of the drive/alignment system included in FIG. 4.

A perspective view of an embodiment of drive/alignment system 42 of FIG. 4 is shown in FIG. 7. In this embodiment, sample stage 40, shown with dashed lines in FIG. 7, is attached to the top of rotation motor 84, which is used to rotate sample stage 40. Rotation motor 84 is situated in y-motion track 86, for movement along the "y" direction by y-motor 88 using y-direction linear translator 90. Y-motion track 86 is in turn situated in x-motion track 92, for movement along the "x" direction by x-motor 94 using x-direction linear translator 96. Motors 84, 94 and 90, actuators 90 and 96, and tracks 86 and 92 are preferably chosen and configured such that topography 48 may be positioned to an accuracy of one micron or less. Other positioning tools, such as piezoelectric elements, may be used in addition to or instead of the motors, actuators and tracks shown in FIG. 7. Motors 94 and 88 may be controlled by computer system 44 (shown in FIG. 4), or may be controlled using a separate motor control unit which communicates with computer system 44. X-motion track 92 is affixed to an upper surface of base plate 98, which should be stable against vibration and allow rigid, stable mounting. A suitable embodiment of base plate 98 may be a massive metal plate with multiple threaded mounting holes, such as a section of an optical table. Base plate 98 may further include vibration isolation elements, such as pneumatic isolators.

Also affixed to base plate 98 in FIG. 7 is mounting fixture 100, which positions alignment light source 102 and alignment photodetector 104 above sample stage 40. Laser 102 and detector 104 are positioned such that a beam of radiation from light source 102 which reflects from the surface of topography 48 is detected by detector 104. The loss of this photodetector signal when topography 48 is moved out of the light source beam may be used to locate the edges of topography 48 during procedures for aligning topography 48. Light source 102 is preferably a semiconductor diode laser, but other compact, narrow-beam light sources may be suitable. The wavelength of light source 102 is not particularly important as long as it is matched to that of detector 104, although a visible beam allows the easiest alignment of the laser/detector/topography system. Detector 104 is preferably a semiconductor diode photodetector chosen to be sensitive to the wavelength of light produced by source 102. Other detector types may be suitable, however, as long as the detector is compact enough to be mounted such that it does not interfere with the movement of topography 48 or the optical path of the Raman spectroscopy measurement. The shape of mounting fixture 100 may be different than that shown in FIG. 7, as long as light source 102 and detector 104 are mounted such that the alignment procedure may be performed, and such that elements 100, 102, and 104 do not interfere with the movement of topography 48 or the Raman spectroscopy measurement. Other parts of drive/alignment system 42 not shown in FIG. 7 include power supplies for light source 102, detector 104, and motors 88 and 94.

Figure 8:
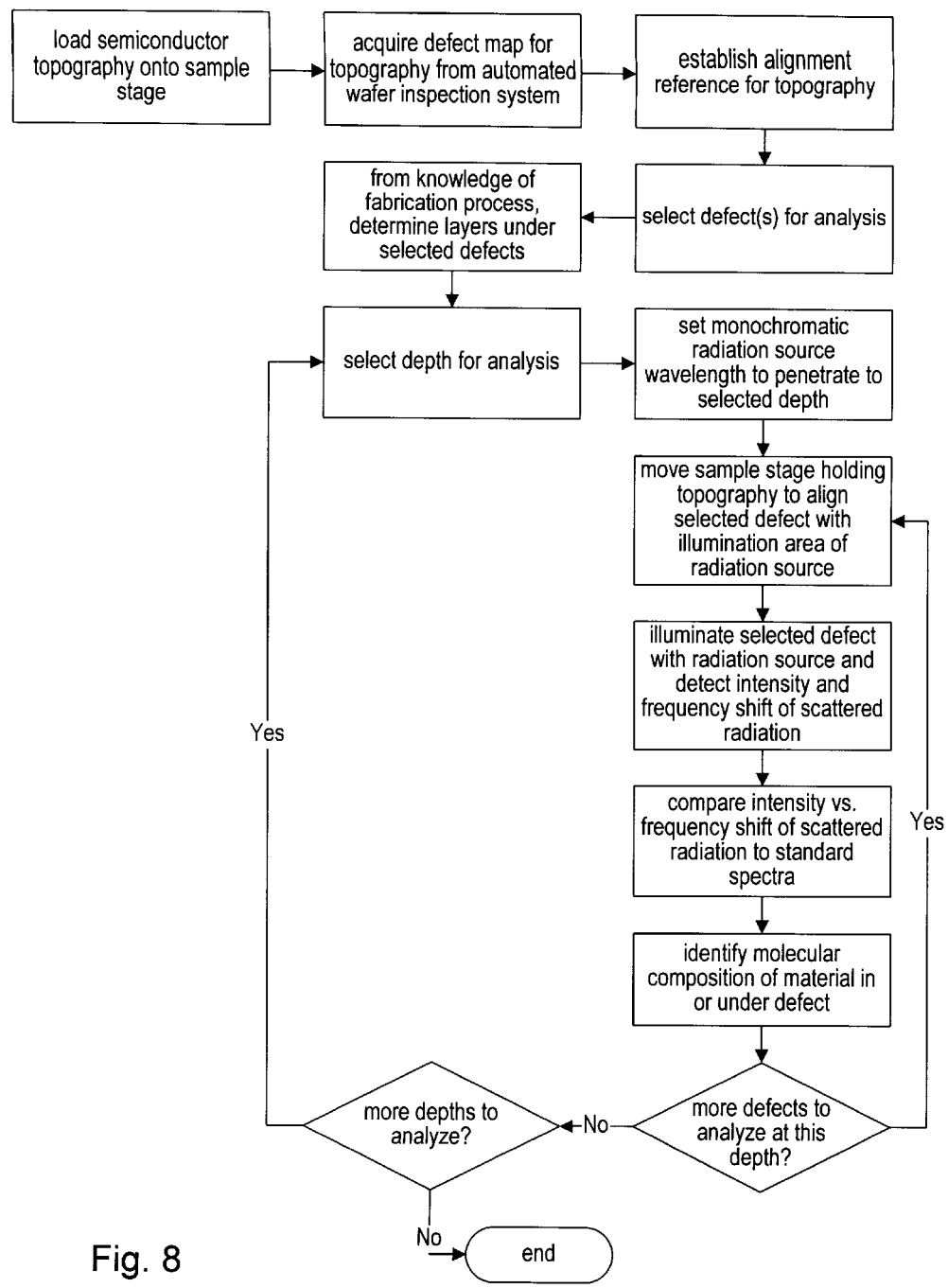
FIG. 8 is a flow diagram of an embodiment of a method for determining the molecular composition of material in or under a defect on a semiconductor substrate.

Turning now to FIG. 8, a flow diagram is shown describing an embodiment of a method for identifying the source of one or more defects arising during a semiconductor manufacturing process. The method of FIG. 8 is described here using apparatus reference labels from FIGS. 4–7. A semiconductor topography, such as topography 48 in FIGS. 4–6 is loaded into a sample holder, such as sample stage 40 in FIGS. 4–6. In this embodiment, a defect map (such as defect map 52 in FIG. 4) for topography 48 has been generated by an automated wafer inspection system, such as 54 in FIG. 4. The defect map is preferably imported into a computer system such as 44 in FIGS. 4–5. Although the defect map must be generated before loading the topography onto the sample stage if defects from the map are to be analyzed, importing the map into computer system 44 may be done before or after loading of the topography. Subsequent to loading the topography onto the sample stage, an alignment reference is established for the substrate. This process, described in more detail in FIGS. 9–13 below, uses drive/alignment system 42 of FIGS. 4, 5, and 7 to establish x-y coordinates for the center of the topography and for a feature cut into the edge of the topography. In the embodiment of FIG. 8, the alignment reference is established after acquiring the defect map and before selecting defects for analysis. Alternatively, the alignment reference may be established at any point in the method of FIG. 8 after the topography is loaded onto the sample stage and before the sample stage is moved to align the first selected defect with the Raman spectroscopy system.

After the defect map of the topography is acquired, one or more defects are selected for analysis. The selected defects are preferably entered into computer system 44. One way in which selected defects may be entered is by selection with a cursor from a displayed image generated by the automated wafer inspection system. Alternative ways that defects may be entered into the computer system include entry of x-y coordinates using a keyboard. After defects are chosen for analysis, knowledge of the fabrication process which has been performed on topography 48 is employed to determine the nominal compositions of layers which may be present under the selected defects. For example, one or more layers may be common to a group of defects having similar appearance. In this way, it may be possible to identify particular steps in the previously-performed fabrication process which are likely to have caused particular defects. From such an identification of likely process steps for origination of a defect, the depth or depths at which useful molecular information may be found is determined. A depth or depths for analysis by Raman spectroscopy is then chosen. In other words, an analysis depth may be chosen by considering intended compositions and thicknesses of layers fabricated below the selected defects during the semiconductor manufacturing process. The wavelength of the monochromatic optical source used, such as optical source 56 in FIG. 5, is then set such that the resulting penetration depth of the optical source matches the desired analysis depth to the extent possible.

Because the region of the topography illuminated by the optical source, shown as region 32 in FIG. 3, extends from the upper surface of the topography to the penetration depth, multiple material layers may contribute to the scattered radiation detected. If the materials contained in the layers are sufficiently different, the intensity peaks arising from different layers may appear in separate portions of the wavenumber scale. In some cases, however, Raman spectra from different layers may interfere with each other. Such interference is often evidenced by features such as broadened peaks or secondary peaks in a spectrum. Intensity features may be localized in depth by comparing spectra taken using various source wavelengths (and thereby various penetration depths). Ways in which the optical source wavelength may be changed include changing the type of laser used, selecting from various output wavelengths available from a laser, or using a tunable laser. Argon ion lasers, for example, provide intense emission at both 514.5 nm and 488 nm, either of which may be used. The major output emission line of a helium-neon laser is at 632.8 nm. Titanium:sapphire solid-state lasers may be tuned to wavelengths between about 675 nm to about 1100 nm. These lasers, combined with other fixed and tunable lasers, allow excitation wavelengths from about 400 nm to about 1100 nm. As noted above, other types of light sources such as lamps combined with wavelength selective elements may also be suitable.

In the embodiment of FIG. 8, the sample stage is moved to align the first selected defect with the illuminated area of the Raman spectroscopy radiation source, after selection of the light source wavelength. The movement is performed using drive/alignment system 42, as discussed further in the description of FIG. 7 above. Scattered radiation is detected by a detector such as detector 74 in FIG. 5, and plotted vs. frequency or wavenumber using computer system 44. The resulting spectrum is subsequently compared to standard reference spectra to aid in identification of the materials within the illuminated volume of topography 48. Additional spectra taken using different penetration depths may be needed for determining the locations of materials identified. In the embodiment of FIG. 8, other defects are analyzed using the same penetration depth before changing the light source wavelength to alter the penetration depth. Alternatively, a range of penetration depths could be used in analyzing one defect before moving the sample stage to align other defects with the Raman spectroscopy system.

In an alternate embodiment, a method similar to that of FIG. 8 may be performed without using a defect map from an automated wafer inspection system. Relatively large defects to be analyzed may be chosen using visual inspection, for example, and aligned with the Raman spectroscopy light source visually using a microscope such as microscope 68 in FIG. 5. Alternatively, regions of topography 48 which do not necessarily contain a defect may be chosen for analysis, in order, for example, to verify the result of a manufacturing process step.

Figure 9:
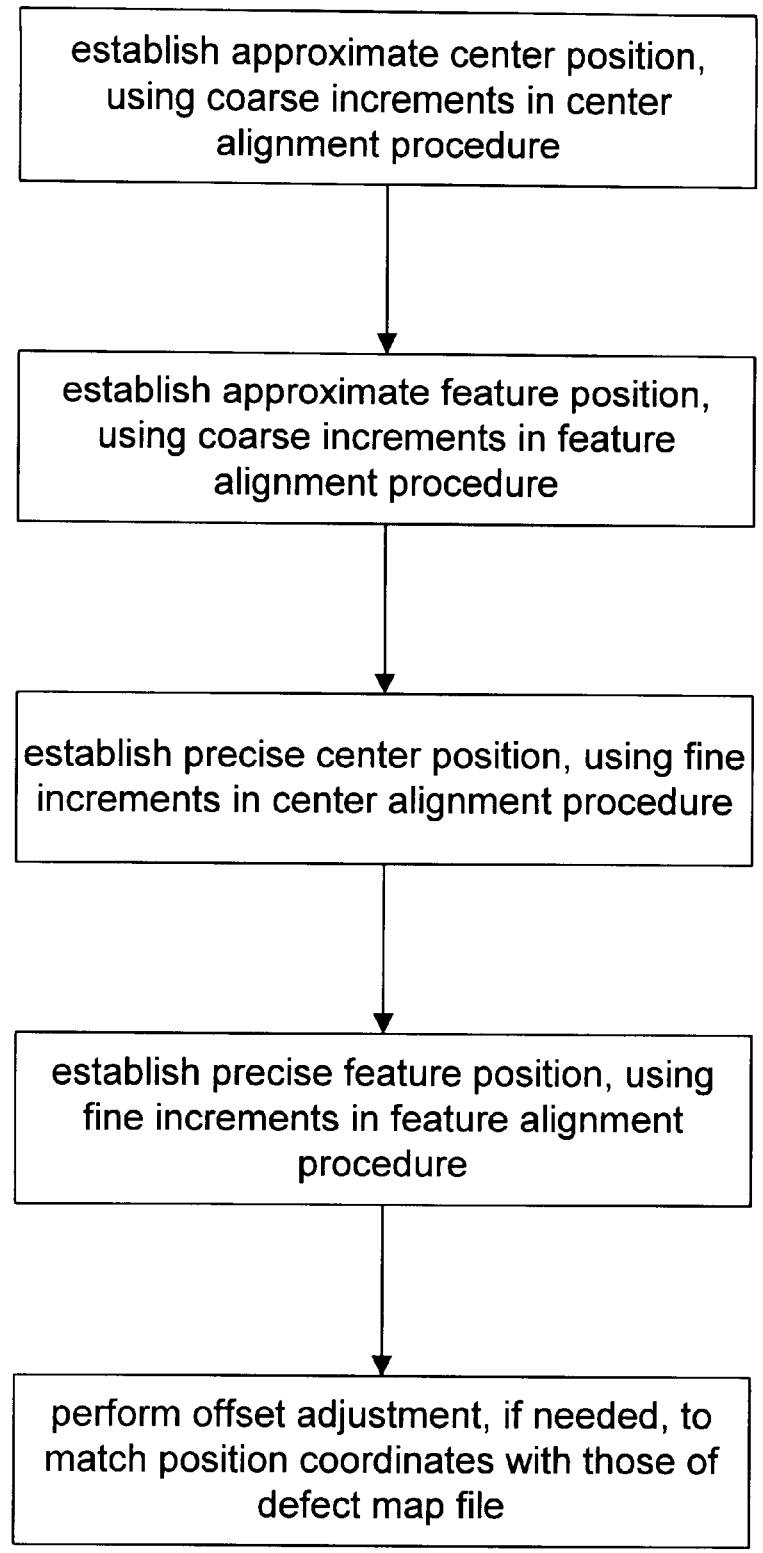
FIG. 9 is a flow diagram of an embodiment of a method for establishing an alignment reference for the substrate, as part of the method shown in FIG. 8.
Figure 10:
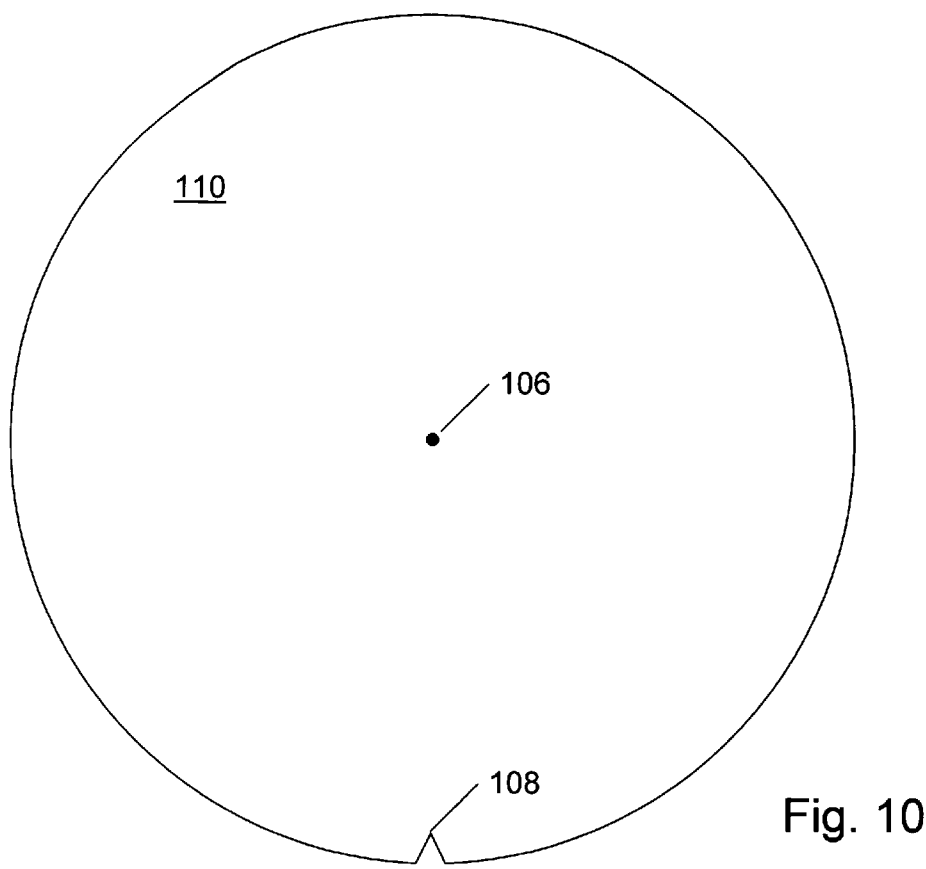
FIG. 10 is a plan view of a semiconductor substrate showing features used for establishing an alignment reference for large substrates.
Figure 11:
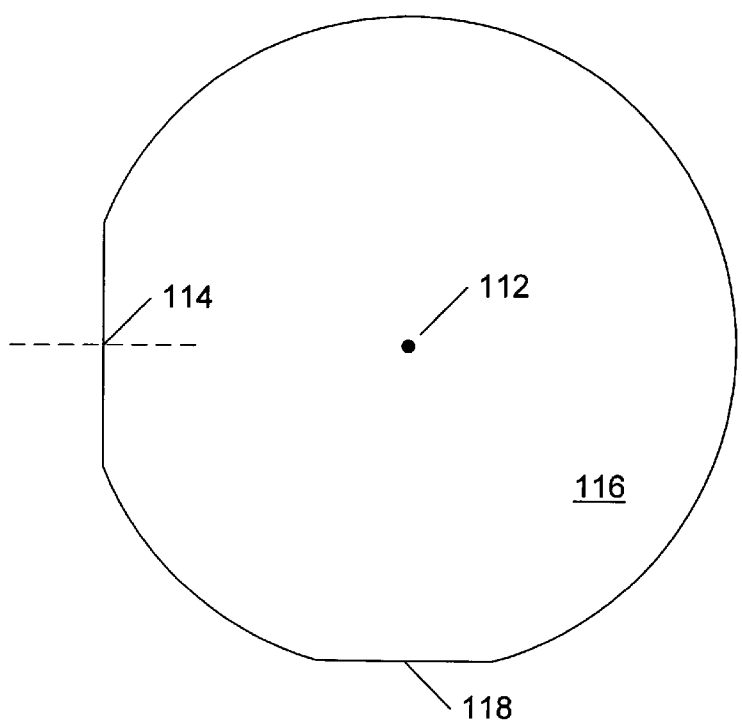
FIG. 11 is a plan view of a semiconductor substrate showing features used for establishing an alignment reference for small substrates.

Turning now to FIG. 9, a flow diagram of a method for establishing an alignment reference for a semiconductor topography is shown. In this embodiment of the method, an approximate center position is established using coarse increments in a center alignment procedure. Such a center alignment procedure is described in more detail in FIG. 12 below. After an approximate center position is established, an approximate position is established for a feature cut into the edge of the semiconductor topography. This feature may take the form of the tip of a notch cut into the edge of the wafer, as is currently typical for 8-inch diameter wafers. Alternatively, the feature may be the midpoint of a flat ground into the edge of the wafer, as is typical for smaller-diameter wafers. Center position 106 and notch tip 108 of 8-inch wafer 110 are shown in FIG. 10, while center position 112 and flat midpoint 114 of smaller wafer 116 (typically a 4- or 6-inch diameter wafer) are shown in FIG. 11. Wafer 116 of FIG. 11 is shown with two flats, as are found on some substrates. Flat 118 is the smaller (i.e., shorter) of two flats, and is known as the "minor flat". The largest of the flats on a wafer is known as the "major flat". The feature used in establishing an alignment reference according to the embodiment of FIG. 9 is further defined to be the midpoint of the major flat on the substrate, for substrates having flats. The approximate feature position is set using coarse increments in a feature alignment procedure, described further in FIG. 13. The approximate center and feature positions are subsequently used as a starting point for establishing accurate center and feature positions. These accurate positions are set using fine increments in center and feature alignment procedures. Finally, in embodiments for which a defect map is imported, an offset adjustment may be performed to match the coordinate system used with that which may be used in the defect map. In alternate embodiments of the method of FIG. 9, additional center and feature positions may be established, having degrees of accuracy intermediate between the approximate and precise positions recited in FIG. 9. Alternatively, a single application of the procedure for center alignment and the procedure for feature alignment may be all that is needed to establish precise center and feature positions, if the initial sample stage mounting is sufficiently accurate.

Figure 12:
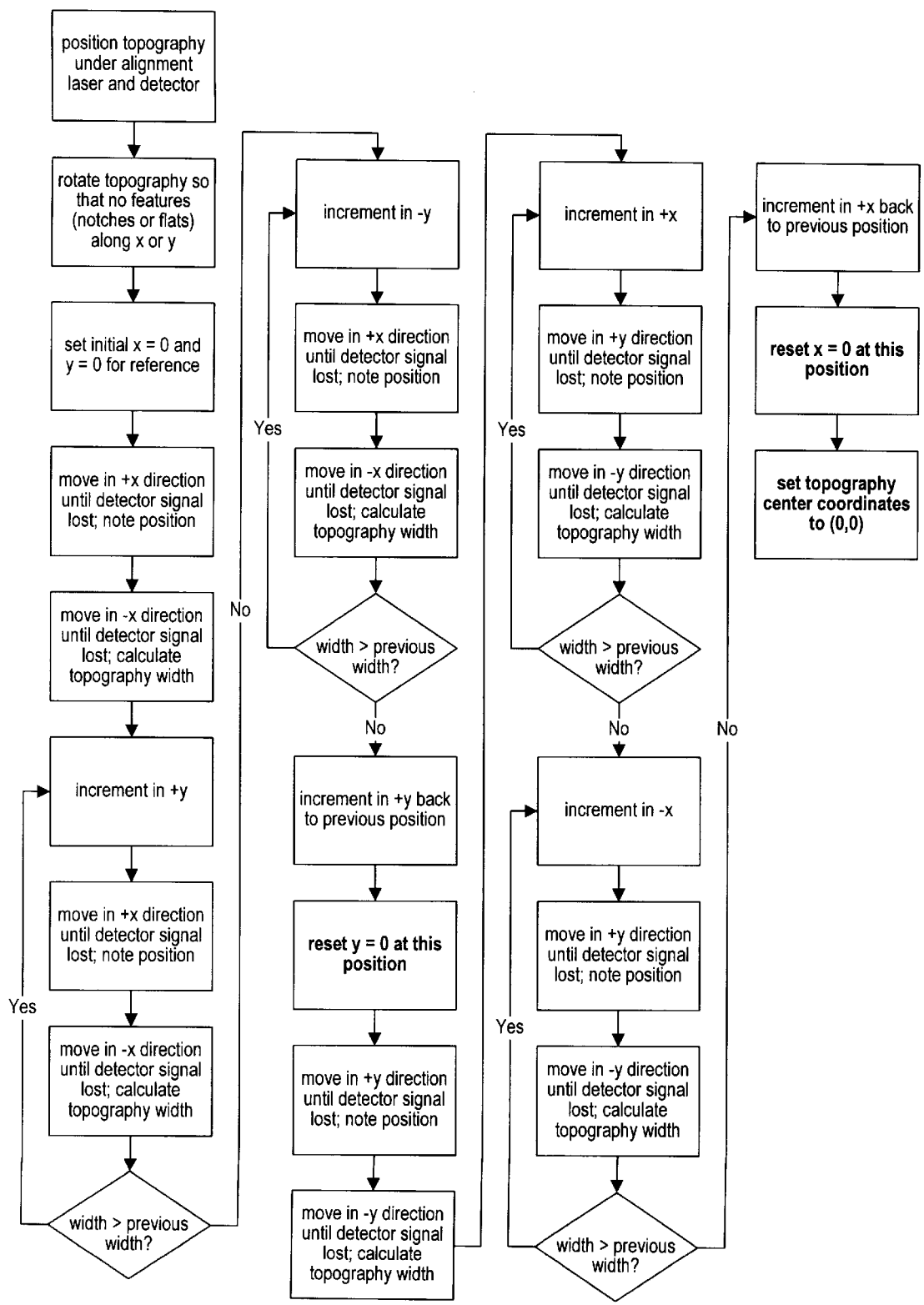
FIG. 12 is a flow diagram of an embodiment of a method for establishing a center position of a substrate, as part of the method of FIG. 9.

An embodiment of the center alignment procedure recited in FIG. 9 is shown in the flow diagram of FIG. 12. This procedure is carried out using drive/alignment system 42 as shown in FIG. 7. Broadly speaking, this embodiment of the procedure works by moving a substrate in the y direction until the largest width of the substrate, or the diameter, in the x direction is found. The y position at which this diameter is found is set to y=0. A similar process of moving the substrate in the x direction to find the diameter along the y-direction is used to set the x=0 position. The increment by which the substrate is moved in either the x or y direction when finding the diameters may be either coarse, to establish the approximate positions recited in FIG. 9, or fine, to establish the accurate positions recited in FIG. 9.

Specifically, the procedure of FIG. 12 begins with positioning the semiconductor topography below an alignment light source (such as 102 in FIG. 7, preferably a laser) and alignment photodetector (such as 104 in FIG. 7) in such a way that radiation from the light source is reflected from the surface of the topography and detected by the photodetector. Adjustment of the light source and photodetector positions may also be needed. Reference to FIGS. 8 and 9 shows that the semiconductor topography is mounted on a sample stage for the procedure of FIG. 12. As noted in the discussion of FIG. 6 above, sample stage 40 may have a diameter larger than that of semiconductor topography 48 in an alternative embodiment. If this is the case, sample stage 40 must be formed such that the radiation from alignment light source 102 is reflected in a substantially different direction from sample stage 40 than from topography 48. In other words, the radiation detected by photodetector 104 must drop abruptly when sample stage 40 is moved such that radiation from light source 102 moves off of topography 48 and onto any adjacent surface of sample stage 40. Otherwise, the edge of topography 48 is not correctly detected.

After the topography is positioned under the alignment light source and photodetector, the topography is rotated such that no edge features of the topography, such as notches or flats, are along the x or y directions (the directions that the x- and y-motors of FIG. 7 move the sample stage). Because the procedure of FIG. 12 relies on finding diameters of the substrate to find the center position, the x and y directions must be along circular portions of the substrate, rather than portions into which features have been cut. The x and y positions at which the topography is initially positioned under the light source and photodetector are initially set to coordinates (0,0), as shown in the flow diagram of FIG. 12. This initial assignment may be performed before or after the topography rotation recited just above it in FIG. 12.

The topography is then moved, using the drive/alignment system, first in the positive x direction and then in the negative x-direction until the photodetector signal is lost. In this way, the edges of the topography are detected, and the width of the topography in the x direction may be calculated. The movement toward a positive x direction first as shown in FIG. 12 is an arbitrary choice; the width may also be calculated by moving first in a negative x-direction. The topography is then moved by an increment in the positive y direction. If the procedure of FIG. 12 is being used to establish an approximate center position as recited in FIG. 9, this increment is relatively coarse (for example, on the order of a millimeter). If an accurate center position is being established, the increment is fine (for example, on the order of a micron). The width of the topography in the x direction is found at the new y-position, and this process is repeated with further increments in y until the calculated width is smaller than the width calculated at the previous y position. The topography is then moved by an increment in the negative y-direction until the diameter in the x direction is found, and the y position for which the diameter is found is set to y=0, as shown in FIG. 12. This y=0 position may also be established by moving the topography first in the negative y direction, and then in the positive y direction.

In the embodiment of FIG. 12, a similar process is subsequently performed to set the x=0 position. The width of the topography along the y direction is found by moving the topography in positive and negative y directions until the alignment detector signal is lost. Successive widths along the y direction are then found as the substrate is moved by increments in the positive x direction. When the width along the y direction becomes smaller than that found at the previous x position, the topography is moved by an increment in the negative x-direction, and the x=0 position is ultimately set at the x position for which the diameter in the y direction is found. As for the process of setting the y=0 position, the x=0 position may also be found by incrementing first in the negative x direction and then in the positive x direction. Furthermore, the x=0 position may be found before the y=0 position, rather than afterwards as shown in FIG. 12. Other techniques of using the drive/alignment system of FIG. 7 to find the center position of the topography may also be suitable.

Figure 13:
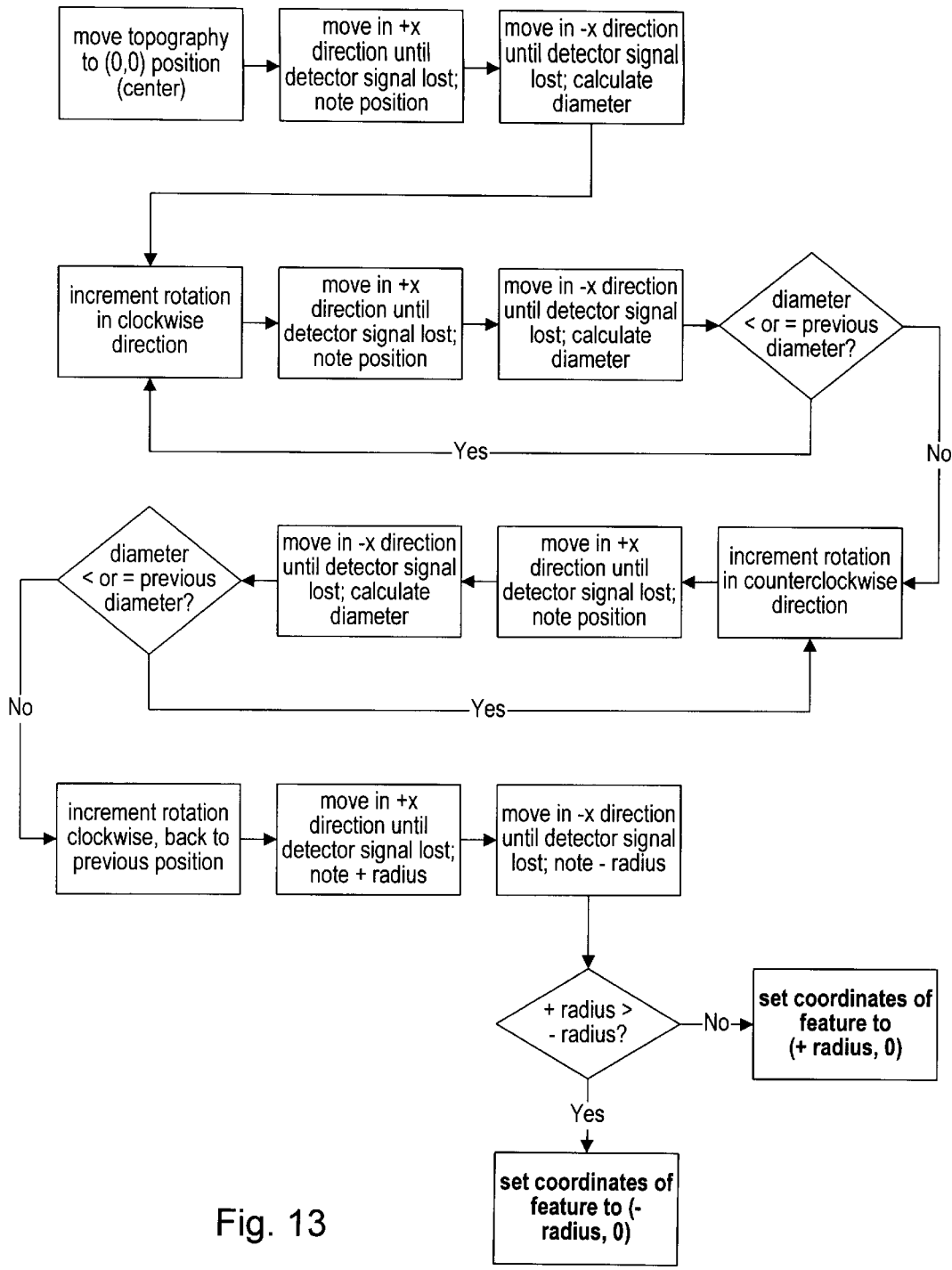
FIG. 13 is a flow diagram of an embodiment of a method for establishing a feature position of a substrate, as part of the method of FIG. 9.

Turning now to FIG. 13, a flow diagram of an embodiment of the feature alignment procedure recited in FIG. 9 is shown. As for the center alignment procedure described above, the procedure of FIG. 13 is performed using drive/alignment system 42. Broadly speaking, the feature position is established by rotating the topography by increments about its center to find the minimum substrate diameter. This minimum diameter is believed to contain the point at which a feature cut into the edge of the substrate penetrates the farthest into the substrate. This point corresponds to the tip of a notch, if a notch is cut into the substrate, or the midpoint of the largest flat which may be ground into the edge of the substrate. In the embodiment of FIG. 13, the feature is aligned along the x direction. The radius of the substrate in the positive x direction is then compared to that in the negative x direction to determine which side of the substrate contains the feature and thereby the x-y coordinates of the feature. In a similar manner as for the center alignment procedure of FIG. 12, the increment used may be coarse when an approximate feature position is being found and fine when a precise position is being established.

Specifically, the semiconductor topography is moved to the (0,0) center position previously established using a center alignment procedure such as that in FIG. 12. Because the feature alignment procedure of FIG. 13 is typically performed soon after a center alignment procedure such as that of FIG. 12, moving the topography to the (0,0) position is believed to also position the topography so that the radiation from alignment light source 102 is reflected by the topography and detected by photodetector 104. In the embodiment of FIG. 13, the topography is then moved first in the positive x direction and then in the negative x direction until the alignment detector signal is lost so that the topography diameter may be calculated. The topography is then rotated by an increment in a clockwise direction, at which position the diameter is again measured in the x direction. The increment may be relatively large, such as on the order of a degree, if an approximate feature position is being established. If a precise feature position is being established, the increment used is typically much finer. To allow an accuracy of about one micron at the edge of an 8-inch wafer, for example, the needed increment is believed to be about two arcseconds. The process of rotating by increments and finding the diameter is repeated until the diameter becomes greater than that measured at the previous rotational increment. The topography is then rotated by an increment in the counterclockwise direction until the minimum diameter is found. At this rotational position, the minimum diameter, and therefore the feature, lies along the x direction. The radius of the substrate in each of the positive and negative x directions is then found, and the smaller radius set to the x-coordinate of the feature.

As in the case of the procedure of FIG. 12, several changes may be made to the procedure of FIG. 13 without altering the utility of the method. For example, the diameter of the topography may be found by moving the topography first in the negative x direction, and the radius of the topography in the negative x direction may be found before that in the positive x direction. Furthermore, the diameter along the y-direction could be found rather than that along the x-direction. In this case, the minimum diameter is ultimately aligned along the y-direction, and the smaller radius becomes the y-coordinate of the feature. In another possible change to the procedure of FIG. 13, the rotational position could be incremented first in a counterclockwise, rather than a clockwise direction. In an alternative embodiment of the procedure of FIG. 13, the topography may already be positioned at the (0,0) position as a result of the center alignment procedure of FIG. 12. Furthermore, the diameter at the (0,0) position may also be known from the center alignment procedure. In this case, the first three steps of the flow diagram of FIG. 13 may be omitted. Other techniques of using the drive/alignment system to find the position of a feature cut into the edge of the topography may also be suitable.

It will be appreciated to those skilled in the art having the benefit of this disclosure that this invention is believed to provide a method and apparatus for molecular identification of material at a selected site on or in a semiconductor topography. Further modifications and alternative embodiments of various aspects of the invention will be apparent to those skilled in the art in view of this description. It is intended that the following claims be interpreted to embrace all such modifications and changes and, accordingly, the specification and drawings are to be regarded in an illustrative rather than a restrictive sense.

What is claimed is:

1. A method for obtaining identification of a molecular composition of material at a selected site within a semiconductor topography, comprising:

determining intended compositions and thicknesses of underlying layers fabricated below the selected site, wherein the determining is accomplished using knowledge of a preceding semiconductor fabrication process performed upon the semiconductor topography;

selecting an analysis depth above which material in the topography is to be identified wherein the analysis depth is consistent with said compositions and thicknesses;

setting a frequency of a monochromatic radiation source such that a penetration depth of radiation from the radiation source into the topography corresponds to the analysis depth;

illuminating the selected site with radiation from the monochromatic radiation source;

detecting intensities and frequency shifts of radiation scattered from an illuminated region of the topography; and comparing the detected intensities and frequency shifts to standard spectra to obtain identification of the molecular composition of the material within the illuminated region.

2. The method as recited in claim 1, wherein said illuminating the selected site further comprises loading the semiconductor topography into a sample stage; and moving the sample stage in a horizontal plane to align the semiconductor topography such that the selected site is illuminated by the monochromatic radiation source.

3. The method as recited in claim 2, wherein said moving further comprises establishing an alignment reference for the sample stage.

4. The method as recited in claim 3, wherein said establishing comprises:

determining x-y coordinates for a center of the topography, wherein the x-y coordinates lie in a horizontal plane;

determining x-y coordinates for a feature cut into an edge of the topography; and assigning x-y coordinates for the semiconductor topography using the center and the feature for reference.

5. The method as recited in claim 4, wherein said determining x-y coordinates for a feature comprises determining x-y coordinates for a notch.

6. The method as recited in claim 4, wherein said determining x-y coordinates for a feature comprises determining x-y coordinates for a center point of a flat.

7. The method as recited in claim 4, wherein said determining x-y coordinates for a center and determining x-y coordinates for a feature comprise using a laser reflection technique.

8. The method as recited in claim 4, wherein said determining x-y coordinates for a center comprises:

positioning an alignment laser and an alignment photodetector above the topography such that radiation from the alignment laser is reflected by the topography and detected by the alignment photodetector;

determining a width of the topography in an x direction by moving the sample stage along positive and negative x directions until the radiation detected by the alignment photodetector abruptly decreases;

determining a y-direction reference position by moving the sample stage in increments along positive and negative y directions and determining the width of the topography in the x direction for each increment, until a maximum width is obtained;

determining an x-direction reference position by moving the sample stage in increments along positive and negative x directions and determining the width of the topography in the y direction for each increment, until a maximum width is obtained; and setting the x-direction and y-direction reference positions to coordinates (0,0), wherein coordinates (0,0) comprise approximate coordinates for the center of the topography.

9. The method as recited in claim 4, wherein said determining x-y coordinates for a feature comprises rotating the topography about coordinates (0,0) and determining the width of the topography for each increment, until a minimum width is obtained.

10. The method as recited in claim 1, wherein said detecting comprises performing a Raman spectroscopy measurement.

11. The method as recited in claim 1, further comprising:

importing a file comprising a defect map of the topography produced by a wafer inspection system into a computer system;

choosing the selected site from among defects in the defect map, prior to said illuminating;

recording intensity versus frequency shift of the radiation scattered from the illuminated region of the topography, subsequent to said detecting; and comparing the intensity versus frequency shift with standard spectra to determine molecular compositions of materials in the illuminated region.

12. The method as recited in claim 11, wherein said illuminating further comprises:

loading the semiconductor topography onto a sample stage;

establishing an alignment reference for the sample stage; and moving the sample stage in a horizontal plane to align the semiconductor topography such that the selected site is illuminated by the monochromatic radiation source.

13. The method as recited in claim 12, wherein said establishing comprises:

determining x-y coordinates for a center of the topography, wherein the x-y coordinates lie in a horizontal plane;

determining x-y coordinates for a feature cut into an edge of the topography;

assigning x-y coordinates for the semiconductor topography using the center and the feature as a reference; and performing an offset adjustment for matching the x-y coordinates with coordinates used by the defect map file.

14. The method as recited in claim 13, wherein said determining x-y coordinates for a center and determining x-y coordinates for a feature comprise using a laser reflection technique.

15. The method as recited in claim 13, wherein said detecting comprises performing a Raman spectroscopy measurement.

* * * * *